(12) United States Patent
Bellussi et al.

(10) Patent No.: US 10,590,356 B2
(45) Date of Patent: Mar. 17, 2020

(54) INTEGRATED PROCESS FOR THE PREPARATION OF COMPOUNDS USEFUL AS FUEL COMPONENTS

(71) Applicant: ENI S.p.A., Rome (IT)

(72) Inventors: Giuseppe Bellussi, Piacenza (IT); Alberto Renato De Angelis, Legnano (IT); Giulio Assanelli, Pavia (IT); Paolo Pollesel, San Donato Milanese (IT)

(73) Assignee: ENI S.p.A., Rome (IT)

( * ) Notice: Subject to any disclaimer, the term of this patent is extended or adjusted under 35 U.S.C. 154(b) by 75 days.

(21) Appl. No.: 14/767,400

(22) PCT Filed: Feb. 11, 2014

(86) PCT No.: PCT/IB2014/058912
§ 371 (c)(1),
(2) Date: Aug. 12, 2015

(87) PCT Pub. No.: WO2014/125416
PCT Pub. Date: Aug. 21, 2014

(65) Prior Publication Data
US 2015/0376523 A1 Dec. 31, 2015

(30) Foreign Application Priority Data
Feb. 14, 2013 (IT) .................. MI2013A0209

(51) Int. Cl.
*C10L 1/18* (2006.01)
*C10L 1/02* (2006.01)
(Continued)

(52) U.S. Cl.
CPC .............. *C10L 1/18* (2013.01); *C07C 29/60* (2013.01); *C07C 41/09* (2013.01); *C07C 45/52* (2013.01);
(Continued)

(58) Field of Classification Search
CPC .......... C07C 19/10; C10L 10/02; C10L 10/04; C10L 10/10; C10L 10/12; C10L 10/16;
(Continued)

(56) References Cited

U.S. PATENT DOCUMENTS

| | | | |
|---|---|---|---|
| 2003/0163949 A1 | 9/2003 | Delfort et al. | |
| 2007/0283619 A1* | 12/2007 | Hillion | C10L 1/026 44/388 |
| 2009/0198088 A1* | 8/2009 | Tirio | B01D 15/185 568/870 |

FOREIGN PATENT DOCUMENTS

| | | | | |
|---|---|---|---|---|
| CN | 102031164 A | * | 4/2011 | |
| EP | 0624563 A1 | * | 11/1994 | C07C 41/01 |

(Continued)

OTHER PUBLICATIONS

Malek. "Simulation of propionaldehyde production from glycerol". 2012.*

(Continued)

*Primary Examiner* — Latosha Hines
(74) *Attorney, Agent, or Firm* — Oblon, McClelland, Maier & Neustadt, L.L.P.

(57) ABSTRACT

The invention relates to an integrated process for the production of fuel components starting from materials of a biological origin which comprises: (A) transformation of glycerine into an alkoxy-propanediol having formula RO—$CH_2$—CHOH—$CH_2$OH, wherein R is a linear or branched $C_1$-$C_8$ alkyl, (B) transformation of glycerine into 1,2-propanediol $CH_3$—CHOH—$CH_2$OH, (C) dehydration of the 1,2-propanediol obtained in (B) to propionic aldehyde, (D) reaction of part of the propionic aldehyde obtained in (C) with the alkoxy-propanediol having formula RO—$CH_2$—CHOH—$CH_2$OH obtained in (A) to give an acetal having formula (a) wherein R is a linear or branched $C_1$-$C_8$ alkyl, (E) transformation of part of the propionic (Continued)

aldehyde obtained in (C) to a propionate having formula $CH_3-CH_2-COOR'$, wherein R' is a linear or branched $C_1$-$C_8$ alkyl. Particular components for gasolines and/or diesel are also described.

11 Claims, 1 Drawing Sheet

(51) Int. Cl.
    *C10L 1/185* (2006.01)
    *C07D 317/22* (2006.01)
    *C07C 45/52* (2006.01)
    *C07C 41/09* (2006.01)
    *C07C 29/60* (2006.01)
    *C07C 67/44* (2006.01)
    *C10L 10/02* (2006.01)
    *C10L 10/04* (2006.01)
    *C10L 10/10* (2006.01)
    *C10L 10/12* (2006.01)
    *C10L 10/16* (2006.01)
    *C10L 1/19* (2006.01)

(52) U.S. Cl.
    CPC ............ *C07C 67/44* (2013.01); *C07D 317/22* (2013.01); *C10L 1/02* (2013.01); *C10L 1/023* (2013.01); *C10L 1/026* (2013.01); *C10L 1/1855* (2013.01); *C10L 10/02* (2013.01); *C10L 10/04* (2013.01); *C10L 10/10* (2013.01); *C10L 10/12* (2013.01); *C10L 10/16* (2013.01); *C10L 1/19* (2013.01); *C10L 2200/0469* (2013.01); *C10L 2270/023* (2013.01); *C10L 2270/026* (2013.01); *Y02P 20/125* (2015.11)

(58) Field of Classification Search
    CPC .. C10L 1/02; C10L 1/023; C10L 1/026; C10L 1/18; C10L 1/1855; C10L 1/19; C10L 2200/0469; C10L 2270/023; C10L 2270/026; Y02P 20/125; Y02P 20/582; C07D 317/22

See application file for complete search history.

(56)     References Cited

FOREIGN PATENT DOCUMENTS

| | | | | |
|---|---|---|---|---|
| EP | 0624563 A1 | * | 11/1994 | ............ C07C 41/01 |
| EP | 1 321 502 A1 | | 6/2003 | |
| WO | WO-2011009936 A2 | * | 1/2011 | ............ C07C 29/60 |

OTHER PUBLICATIONS

Malek. "Simulation of propionaldehyde production from glycerol". 2012 (Year: 2012).*
International Search Report and Written Opinion dated May 9, 2014 in PCT/IB2014/058912.

* cited by examiner

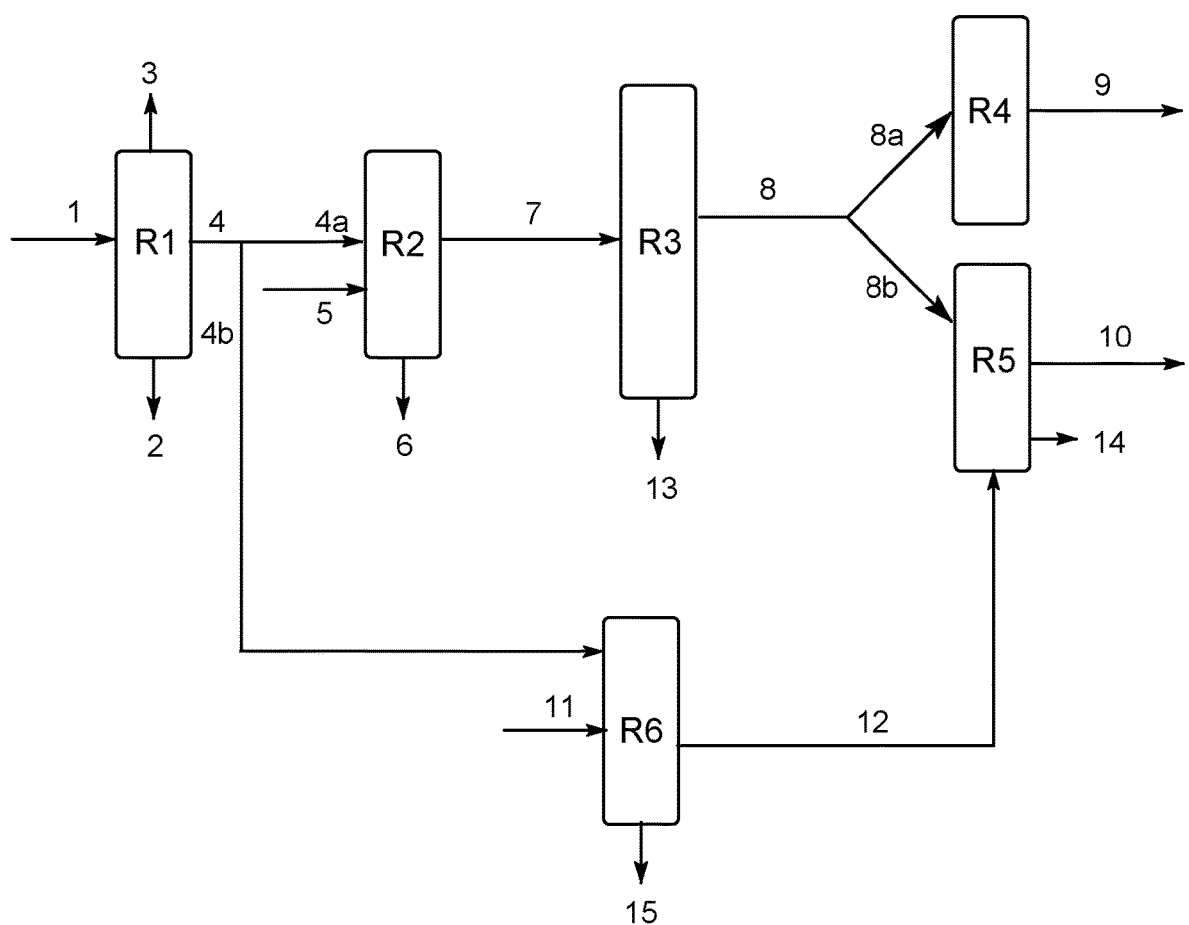

INTEGRATED PROCESS FOR THE PREPARATION OF COMPOUNDS USEFUL AS FUEL COMPONENTS

CROSS-REFERENCE TO RELATED APPLICATIONS

This application is a National Stage of PCT/IB2014/058912, which was filed on Feb. 1, 2014. This application is based upon and claims the benefit of priority to Italian Application No. MI2013A 000209, which was filed on Feb. 14, 2013.

The present invention relates to an integrated process for the production of components for diesel or gasolines starting from materials of a biological origin. Particular components for these fuels are also described.

It is known that the emissions produced by the combustion of fuels of a fossil origin containing carbon dioxide ($CO_2$), carbon monoxide (CO), nitrogen oxides ($NO_x$), sulfur oxides ($SO_x$), uncombusted hydrocarbons (HC), volatile organic compounds and particulate (PM), are the cause of environmental problems such as, for example, the production of ozone, the greenhouse effect in the case of nitrogen and carbon oxides and acid rain in the case of sulfur and nitrogen oxides.

In recent years, the increase in the cost of crude oil and a maturing awareness with respect to the environmental problems described above, have increased the necessity for finding alternative, biodegradable and renewable energy sources. Consequently, the progressive substitution of fuels deriving from fossil energy sources such as, for example, coal, petroleum, natural gas, with fuels deriving from alternative energy sources such as, for example, vegetable oils, animal fats, biomasses, algae, is becoming of increasing interest on a worldwide scale and efforts have therefore been made in the art to obtain new fuels from renewable energy sources.

An oxygenated compound, that can also be obtained from renewable sources, normally added to fuels, is ethanol, which however has the defect of being miscible with water, hygroscopic, and immiscible with gasoil within a wide temperature range: phase separation can therefore take place and the mixtures obtained are unstable, as described, for example, by Lapuerta et al. in the article "Stability of diesel-bioethanol blends for use in diesel engines", published in "Fuel" (2007), Vol. 86, pages 1351-1357. Another alcohol, that can also be obtained from renewable sources, which can be used as component to be added to fuels, is butanol, which has a better miscibility with gasoil with respect to that of ethanol: it is still unsatisfactory, however. At low temperatures, in fact, butanol-gasoil blends are not homogeneous. A further problem linked to the use of these alcohols is the low cetane number of the alcohol-gasoil blend which causes a high ignition delay in internal compression diesel engines.

The use is also known of biodiesel and hydrotreated vegetable oils (HVO) as such, or in a blend with gasoil. Biodiesel generally comprises a blend of fatty acid alkyl esters, in particular a blend of fatty acid methyl esters (FAME) and can be produced starting from raw materials of a natural origin containing triglycerides (generally triesters of glycerol with fatty acids having a long alkyl chain). Said raw materials as such, or the triglycerides obtained after subjecting said raw materials to separation, are subjected to a transesterification process in the presence of an alcohol, in particular, methanol, and a catalyst, in order to obtain said fatty acid alkyl esters, in particular said fatty acid methyl esters (FAME). The use of these fatty acid methyl esters (FAME), however, as such, or in a mixture with gasoil, has various problems relating to the oxidation stability and also during the synthesis of FAME, there is the formation of glycerine (about 10% by weight) as by-product, whose use is an important aspect for upgrading the production process of biodiesel.

The use is also known of hydrotreated vegetable oils (HVO), also called green diesel, which are produced by the hydrogenation/deoxygenation of a material deriving from renewable sources, such as, for example, soybean oil, rape oil, corn oil, sunflower oil, comprising triglycerides and free fatty acids, in the presence of hydrogen and a catalyst as described, for example, by Holmgren J. et al. in the article "New developments in renewable fuels offer more choices", published in "Hydrocarbon Processing", September 2007, pages 67-71. This article indicates the best characteristics of said hydrotreated vegetable oils (HVO) with respect to fatty acid methyl esters (FAME), in particular, in terms of a better oxidation stability and improved cold properties. Furthermore, said hydrotreated vegetable oils (HVO) do not have the problem of greater emissions of nitrogen oxides ($NO_x$). Due to the lack of oxygen atoms in said hydrotreated vegetable oils (HVO), however, their use in diesel engines mixed with gasoil in an amount lower than 5% by volume with respect to the total volume of said mixture, does not provide significant benefits with respect to particulate emissions (PM).

The necessity is therefore felt for finding new compositions useful as fuels, in which there is a component deriving from renewable energy sources. The necessity is also felt for exploiting glycerine, whose market is currently saturated, as a starting material for obtaining compounds of a biological origin which can provide high performances as fuel components. At present, one of the possible uses of glycerine is to react it, by means of an etherification reaction, with olefins to give the corresponding ethers, which can be used as oxygenated components for gasoline and diesel. The olefin mainly used and object of numerous patents is isobutene. The reaction with isobutene leads to the formation of tert-butyl ethers of glycerine, of which the most interesting is di-tert-butyl ether. In these ethers, however, the biological component is clearly a minority as they consist of two, or rather three, molecules of isobutene per molecule of glycerine: consequently, their contribution in reaching the quota of a biological origin is not sufficiently high.

US2007/0283619 describes a process for the production of biofuels by the transformation of triglycerides into at least two groups of biofuels containing fatty acid monoesters and soluble ethers or acetals of glycerine. Said ethers and acetals of the known art, however, have a high affinity with water and a low miscibility with the hydrocarbon phase: this is a serious limitation for their use as fuel component as significant quantities of water can dissolve in the mixture of fuels containing said acetals, with considerable damage to the engine of the motor vehicle due to corrosion phenomena. Furthermore, the presence in gasolines of substances miscible with water leads to the formation of formaldehyde, a carcinogenic substance, in the emissions (B. Strus et al., Fuel 87 (2008), 957-963, ELSEVIER).

MI 2012A000570 describes compositions containing:
a hydrocarbon mixture,
at least one ketal or cyclic acetal selected from those having formula (I) and (II):

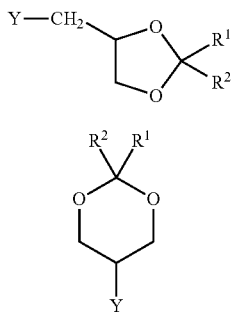

wherein $R^1$ is a linear or branched alkyl containing from 1 to 6 carbon atoms, possibly substituted by an alkoxide group OR, wherein R is an alkyl containing from 1 to 4 carbon atoms, $R^2$ is H or a linear or branched alkyl containing from 1 to 6 carbon atoms, possibly substituted by an alkoxide group OR, wherein R is an alkyl containing from 1 to 4 carbon atoms, $R^2$ is the same as or different from $R^1$, Y is selected from H or $OR^3$, $R^3$ being a linear or branched alkyl containing from 1 to 8 carbon atoms.

The addition of ketals or acetals described above to suitable hydrocarbon mixtures allows a composition to be obtained which can be advantageously used as fuel, in particular as fuel for both diesel and gasoline engines.

Said ketals or acetals are prepared through the following steps:

(1) transformation of glycerine into propanediol or alkoxy-propanediol (2) reaction of the diol obtained in step (1) with a carbonyl compound selected from aldehydes and ketones to give the corresponding cyclic acetal having formula (I) or (II).

MI 2012A002006 describes compositions containing:

at least one hydrocarbon mixture, at least one compound having formula $X-CH_2-A-(B)_y-OR$ wherein X is selected from H and OR, R is a $C_1-C_8$ alkyl, A and B are different from each other and are selected from $CH_2$ and CO, y is selected from 0 and 1.

The addition of the hydrophobic oxygenated compounds described above to suitable hydrocarbon mixtures allows a composition to be obtained which can be advantageously used as fuel, in particular as fuel for both diesel and gasoline engines.

In the particular case of compounds having formula $X-CH_2-A-(B)_y-OR$ (I), wherein X is H, R is a $C_1-C_8$ alkyl, A is $CH_2$, B is CO and y is 1, their preparation comprises the following steps:

catalytic reduction of glycerine to 1,2-propanediol (a1)
dehydration of (a1) to propionic aldehyde (a2)
oxidation of (a2) to propionic acid (a3)
esterification of (a3) with an alcohol ROH, wherein R is a $C_1-C_8$ alkyl, to give $CH_3-CH_2-COOR$ (Ia).

The Applicant has now found an integrated process for the contemporaneous preparation of particular acetals and propionic esters which provide high performances as fuel components, also overcoming the known problems of ethers of glycerine with respect to their high affinity with water and low affinity with the remaining hydrocarbon component of the fuel. The compounds thus obtained have high characteristics with respect to the octane number (or cetane number), a high calorific power, complete miscibility with the hydrocarbon phase and a very low affinity with the aqueous phase, they are consequently not hygroscopic and therefore reduce problems associated with miscibility and corrosion of parts of the engine due to the presence of traces of water. These compounds, either individually or in a mixture with each other, can therefore be advantageously used as fuel components, in particular gasoil, especially for automotive use, and as additives for gasoline, and their addition to gasoil or gasoline allows, inter alia, a significant decrease in particulate emissions. The composition containing them is less sensitive to the presence of water and consequently there is a significant reduction in corrosion phenomena in the engines. The addition of the compounds, moreover, has no negative influence on the characteristics of the starting gasoil such as, for example, the cold properties, cloud point (CP) and cold filter plugging point (CFPP), neither does it negatively influence the demulsification characteristics and lubricity properties of the composition, nor does it have a negative influence on the oxidation stability of the starting gasoil.

According to the legislation in force, the integrated process of the present invention therefore allows fuel components to be prepared, starting from compounds of a biological origin, in particular glycerine. The process scheme of the present invention can be applied to any type of refinery, possibly re-using existing reactors and equipment. The integrated process of the present invention allows various types of fuel components to be obtained contemporaneously, whose proportion can be varied according to market demands and requirements.

An object of the present invention therefore relates to an integrated process for the production of components for fuels, in particular diesel or gasolines, starting from materials of a biological origin. In particular, said integrated process comprises:

(A) transformation of glycerine into an alkoxy-propanediol having formula $RO-CH_2-CHOH-CH_2OH$, wherein R is a linear or branched $C_1-C_8$ alkyl, (B) transformation of glycerine into 1,2-propanediol $CH_3-CHOH-CH_2OH$, (C) dehydration of the 1,2-propanediol obtained in (B) to propionic aldehyde, (D) reaction of part of the propionic aldehyde obtained in (C) with the alkoxy-propanediol having formula $RO-CH_2-CHOH-CH_2OH$ obtained in (A) to give an acetal having formula (a)

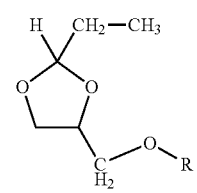

wherein R is a linear or branched $C_1-C_8$ alkyl, (E) transformation of part of the propionic aldehyde obtained in (C) to a propionate having formula $CH_3-CH_2-COOR'$, wherein R' is a linear or branched $C_1-C_8$ alkyl.

According to the process of the invention, the propionaldehyde obtained from the transformation (C) is partly fed to the transformation (D) and for the remaining part is fed to the transformation (E): the quantities fed to the two transformations can be calibrated as desired, depending on the final component, propionate or acetal (a), which is to be obtained in a greater quantity, according to market requirements. According to a preferred aspect of the invention, from 1 to 99% of the propionaldehyde produced in (C) can be fed to the transformation (D) and the remaining part of the propionaldehyde, therefore varying within the range of 99 to 1%, is contemporaneously fed to oxidation (E). Preferably from 40 to 60% of the propionaldehyde produced in (C) can be fed to the transformation (D) and the remaining part of propionaldehyde, therefore varying within the range of 60 to 40%, is contemporaneously fed to oxidation (E).

A preferred aspect of the present invention is that the substituent R of the acetal having formula (a) is selected from $CH_3$, $C_2H_5$, $C_3H_7$, $C_4H_9$, $C_5H_{11}$. A preferred aspect of the present invention is that the substituent R' is selected from $CH_3$, $C_2H_5$, $C_3H_7$, $C_4H_9$, $C_5H_{11}$.

More preferably, R and R' can be independently selected from ethyl, n-propyl, iso-propyl, n-butyl, isobutyl, sec-butyl, tert-butyl, 3-methyl-1-butyl and 2-methyl-1-butyl.

A particularly preferred aspect is that R and R' are independently ethyl, n-propyl, iso-propyl or n-butyl.

The transformation (A) of glycerine into an alkoxypropanediol having formula RO—$CH_2$—CHOH—$CH_2OH$, wherein R is a $C_1$-$C_8$ alkyl, corresponds to the etherification of glycerine, wherein said etherification is effected by reaction with an alcohol having formula ROH to give the corresponding 3-alkoxy-1,2-propanediol. The etherification can be effected according to any of the known methods for the preparation of ethers. The glycerine can be reacted, for example, in the presence of the alcohol and an acid catalyst. Acid catalysts which can be conveniently used are, for example, acid exchange resins, acid zeolites, silico-aluminas, supported phosphoric acid. The acid exchange resins can be used directly in the form of microspheres, as normally supplied by the producer, the acid zeolites and silico-aluminas are preferably extruded using any known ligand, for example, alumina. Solvents which can be conveniently used are preferably the same alcohols with which the corresponding ether is to be formed. The reaction is preferably carried out at a temperature ranging from 50 to 200° C., and a pressure ranging from 1 to 20 atmospheres. The space velocity preferably ranges from 0.1 to 20 $hours^{-1}$. The alcohol/glycerine molar ratio preferably ranges from 1 to 10. The etherification in position 1 is favoured, using a fixed-bed reactor, by the selection of low contact times. The feeding of the reagents to the reactor can be effected in countercurrent and in direct current.

ROH alcohols which can be conveniently used for the etherification are alcohols in which R is a linear or branched alkyl containing from 1 to 8 carbon atoms, preferably from 2 to 4 carbon atoms. Alcohols which can be conveniently used are therefore ethanol, n-butanol, iso-butanol, 3-methyl-1-butanol, 2-methyl-1-butanol, or mixtures thereof. Ethanol or n-butanol are preferred.

Alcohols which can also be obtained biologically are preferably used, i.e. that can be obtained, for example, by the fermentation of biomasses or biomass derivatives, or by the fermentation of biomasses deriving from agricultural crops rich in carbohydrates and sugars, or by the fermentation of lignocellulosic biomasses, or by the fermentation of algal biomasses. The lignocellulosic biomass can derive from agricultural crops rich in carbohydrates and sugars, such as, for example, corn, sorghum, barley, beet, sugar cane, or mixtures thereof. The lignocellulosic biomass can be selected, for example, from:

products of crops expressly cultivated for energy use (such as, for example, miscanthus, switchgrass, foxtail millet, common cane), including waste products, residues and scraps of said crops or their processing;

products of agricultural cultivations, forestation and silviculture, comprising wood, plants, residues and waste products of agricultural processing, forestation and silviculture;

waste of agro-food products destined for human nutrition or zootechnics;

residues, not chemically treated, of the paper industry;

waste products coming from the differentiated collection of solid urban waste (e.g. urban waste of a vegetable origin, paper, etc.);

or mixtures thereof.

The alcohol used can, for example, also derive from the fermentation of at least one algal biomass cultivated for energy purposes, or from the fermentation of residues or derivatives from the cultivation of said biomass.

The fermentation can be effected according to methods known in the art. Said fermentation, for example, can be carried out in the presence of natural microorganisms, or microorganisms genetically modified for improving said fermentation.

The transformation (B) for the reduction of glycerine is effected according to any of the known methods for the reduction of hydroxyl groups. The glycerine, for example, can be reacted with hydrogen in the presence of a reduction catalyst. Reduction catalysts that can be used, can be all known reduction catalysts, for example copper chromite, mixed chromium-zinc-copper oxides, noble metals on carbon, noble metals on iron oxide; platinum on carbon or copper chromite are preferably used, the latter catalyst being particularly preferred. The catalyst consisting of copper chromite can be used as a powder, compressed and sieved; the supported noble metal can be used either as a powder or as an extruded product. Solvents which can be used are linear aliphatic alcohols or the same diol to be obtained as product. The reduction reaction can be carried out at a temperature ranging from 100 to 300° C., under a hydrogen pressure ranging from 1 to 100 atmospheres. The 1,2-propanediol is then isolated, for example by distillation. A fixed bed of catalyst is preferably used and the feeding of the reagents can be effected either in direct current or countercurrent. Other reaction systems such as ebullated beds can also be advantageously used.

Further details relating to reduction processes are described, for example, in "Selective hydrogenolysis of glycerol promoted by palladium", Green Chemistry 2009, 111, 1511-13.

The transformation (C) by dehydration of 1,2-propanediol to propionaldehyde can be effected by feeding the 1,2-propanediol onto a solid acid catalyst, preferably in vapour phase. The reaction is carried out by feeding the propanediol at a temperature ranging from 200 to 350° C., as such or in a stream of nitrogen, in this latter case operating at a propanediol/nitrogen molar ratio ranging from 0.1 to 10. The pressure preferably ranges from 0.1 to 10 atmospheres. All inorganic solid acids, such as aluminas, silico-aluminas, zeolites and oxides having dehydrating properties, such as cerium (IV) oxide, thorium oxide, zirconia, can be used as dehydration catalysts. Among dehydration catalysts, aluminas, Beta zeolite and Y zeolite are particularly preferred. The zeolites can be used in extruded form, using any of the known ligands, preferably alumina, whereas the other dehydrating materials described above can be used either as compressed and sieved powders and as extruded products: in the latter case, the ligand used will depend on the choice of dehydrating material used. Further details relating to reduction processes are described, for example, in "Catalytic dehydration of 1,2 propandiol into propanal", Applied catalysis A, 366, 2009, 304-8, and in "Dehydration of 1,2 propandiol to propionaldehyde over zeolite catalysts", Applied catalysis A, 400, 2011, 148-155.

According to the reaction (D), the alkoxy-propanediol obtained in (A) is reacted with part of the propionic aldehyde obtained in (C) to give the corresponding acetal having formula (a). The formation reaction of the acetal is effected in the presence of an acid catalyst, according to known formation methods of acetals and ketals.

Catalysts which can be conveniently used are acid exchange resins, zeolites, silico-aluminas. When the catalyst used consists of exchange resins, it can be used in the form of microspheres, as supplied by the producer. When the catalyst consists of another type of solid acid, it is preferably in extruded form with a suitable ligand, for example alumina. The same ketones or aldehydes, used in excess, can be adopted as solvents. The molar ratio between aldehyde, or ketone, and diol preferably ranges from 1/1 to 10/1 and even more preferably from 3/1 to 5/1. Reaction temperatures which can be conveniently used range from −10° C. to 120° C. and even more preferably from 20 to 80° C. The pressure preferably ranges from 0.1 to 20 atmospheres. Further details relating to formation processes of acetals which can be used in the preparation process of the present invention are described, for example, in J. Deutsch, A. Martin, H. Lieske, Investigation on heterogenuously catalysed condensation of glycerol to cyclic acetals, Journal of catalysis, 245, 2007, 428-35.

As better described hereunder, the acetals having formula (a) obtained from the reaction (D) can be used as components of compositions useful as fuels: these compositions contain said acetals and hydrocarbon mixtures suitable for being used as fuels, particularly gasoil, gasoline, biodiesel, green diesel, and mixtures thereof.

The acetals having formula (a) are preferably used as components of diesel fuels. In particular the acetals having formula (a) wherein R is $CH_3$, $C_3H_7$, $C_4H_9$ are new as also the fuel compositions containing them.

The transformation (E) can be effected in various ways. The propionic aldehyde, for example, can be oxidized to the corresponding propionic acid which is then esterified with a $C_1$-$C_8$ alcohol. In this case, the oxidation can be effected with any oxidation catalyst, preferably with a catalyst containing metals of group VIB of the periodic system, for example Cr, Mo, W, in a mixture with metals of group VB, for example V. Catalysts containing metals of group VIII of the periodic system such as iron, cobalt or nickel can also be conveniently used. Non-metallic oxidants such as, for example $SeO_2$, can also be used. The metals Mo—V both as mixed oxides and as heteropolyacids, are particularly preferred. The reaction is carried out at temperatures ranging from 20 to 100° C., in the presence of air, enriched air, oxygen or hydrogen peroxide, in a molar ratio aldehyde/oxidant ranging from 1/1 to 1/10. Further details relating to oxidation processes are described, for example, in "Montmorillonite clay-catalyzed oxidation of aliphatic aldehydes", Tetrahedron Letters, 51, 2010, 826-7 and in "Selenium oxide catalysed oxidation of aldehydes to carboxylic acids with hydrogen peroxide", Synthetic Communications, vol. 30, 24, 2010, pages 4425-34.

The esterification of the propionic acid thus obtained with the alcohol ROH to give the corresponding propionic ester is effected according to any of the known methods, for example, by reacting the propionic acid and alcohol in a molar ratio of 1/1, at a temperature ranging from 25 to 100° C., at atmospheric pressure, in the presence of a strong mineral acid such as, for example, sulfuric acid and ferric sulfate, according to what is described in "$Fe(SO_4)_3$ $4H_2O$—$H_2SO_4$: an efficient catalyst for etherification", Journal of Chemical research, 2004(3), 2004, 226-27. Alternatively, a solid acid selected from zeolites, heteropolyacids and acid exchange resins, can be used. The zeolites can be used as extruded products, preferably using alumina as ligand, whereas the other dehydrating materials described above, heteropolyacids and resins, can be used either as compressed and sieved powders and as extruded products, in this case using a ligand which depends on the choice of dehydrating material used. In particular, according to a particularly preferred embodiment, the propionaldehyde can be reacted with a solid base catalyst according to the Tishchenko reaction to give the corresponding propyl propionate in a single step. The Tishchenko reaction is preferably carried out under the following general conditions: aluminium alcoholates having general formula $Al(OR)_3$ are used as catalysts, wherein R is a linear or branched alkyl group ranging from $C_2$ to $C_6$, or basic solids such as magnesium oxide, calcium oxide, strontium oxide, barium oxide, zinc oxide, or hydrotalcites having general formula $M^{2+}{}_aM^{3+}{}_2(OH)_{16}X.nH_2O$, wherein $M^{2+}$ is a bivalent metal cation selected from $Mg^{2+}$, $Fe^{2+}$, $Ni^{2+}$, $Zn^{2+}$, $Cd^{2+}$ and $Co^{2+}$, $M^{3+}$ is a trivalent metal cation selected from $Al^{3+}$, $Fe^{3+}$, $Ga^{3+}$, $Cr^{3+}$, $Mn^{3+}$ and $Co^{3+}$, X is an anion selected from $CO_3{}^{2-}$, $OH^-$ and $NO^{3-}$ and a is an integer ranging from 10 to 4. Another type of preferred catalyst for the Tishchenko reaction are basic zeolites, or zeolites partially or completely exchanged with alkaline metals such as sodium, potassium, rubidium, caesium. Preferred zeolites are zeolite Y, beta zeolite and the zeolite ZSM-5.

The zeolites can be used as an extruded product, preferably adopting alumina as ligand, whereas the other catalysts described above can be used either as compressed and sieved powders and as extruded products, in this case, using a ligand which depends on the choice of catalytic material used. The Tishchenko reaction on propionaldehyde to give propyl propionate is carried out at temperatures ranging from −20 to 150° C., and more preferably from 0 to 100° C. The reaction pressure ranges from 0.1 to 50 bar and more preferably from 1 to 10 bar. Further details relating to processes for carrying out the Tishchenko reaction are provided, for example, in "The Tishchenko reaction and its modifications in organic synthesis" Recent Research Development Organic Chemistry, volume 5, 2001, pages 225-255 and in "Heterogeneuous Basic Catalysis" Chjemistry Review, 1995, volume 95, pages 537-558.

The propionates having formula $CH_3CH_2COOR'$, and in particular propyl propionate, can be used as fuel components, for both gasoline and diesel, and are preferably used as components for gasolines.

As indicated above, a particularly advantageous aspect of the integrated process of the present invention is its versatility: said process allows both components for gasolines and components for diesel to be obtained, in variable reciprocal quantities as desired, and therefore in quantities that can be oriented and selected according to market requirements.

The glycerine used in both the transformation (A) and transformation (B) can be previously purified of the salts and excess water which may be present if it derives from the transesterification of triglycerides. According to a preferred aspect, the raw glycerine deriving from these processes (80-85%), before being used in the integrated process of the present invention, is subjected to a purification pretreatment for obtaining glycerine having a purity of at least 98%. Said purification can be effected for example by means of a process comprising two steps:

in the first step, the salts contained in the raw glycerine, coming from the production of FAME, are removed by treatment on acid exchange resins such as Amberlyst 15, Amberlyst 36, the removal preferably being effected at temperatures ranging from 0 to 60° C. and even more preferably from 15 to 30° C., operating at atmospheric pressure;

in the second step, the impurities present in the raw glycerine, prevalently consisting of water with small quantities of methanol, are removed by fractionated distillation until a glycerine content of at least 95-96% is obtained.

Further details relating to the purification of glycerine are provided, for example, in "PERP Report Glycerin conversion to propylene glycol 06/07S4, March 2008". The glycerine resulting from the steps described above can be used in the process of the present invention without any further purification.

FIG. 1 shows a scheme example relating to the integrated process of the present invention. According to said scheme, the charge of raw glycerine, normally having a purity ranging from 80 to 85%, is fed through line 1 to the purification area R1. The purification of the glycerine is effected in this area by means of exchange resins with the removal of salts through line 2, and the water contained in the glycerine is separated by distillation, removing it through line 3. The purified glycerine, exiting through line 4 from the area R1, is divided into two streams: one stream is fed through line 4a to the area R2 and the other is fed through line 4b to the area R6. The transformation of glycerine into 1,2-propanediol takes place in the area R2 by reduction with hydrogen, fed through line 5. the water which is formed as by-product is removed through line 6 and the 1,2-propanediol is fed through line 7 to the area R3. The dehydration of 1,2-propanediol to propionic aldehyde takes place in the area R3, with the formation of water which is removed through line 13. The propionic aldehyde, leaving the area R3 through line 8, is divided into two streams: one stream is fed to the area R4 through line 8a and the other stream is fed to the area R5 through line 8b. The direct transformation of the propionic aldehyde to propyl propionate takes place in the area R4 by means of the Tishchenko reaction: the propionate is then recovered through line 9. The purified part of glycerine fed through line 4b is transformed in the area R6 to alkoxy-propanediol by reaction with the corresponding alcohol fed through line 11, the water, which is removed through line 15, is then separated from the alkoxy-propanediol, which is sent to the area R5, through line 12. The other part of propionaldehyde deriving from R3 reacts, in the area R5, with the alkoxy-propanediol to give the corresponding acetal which is recovered through line 10, whereas the water formed as by-product is removed through line 14.

As previously indicated, the compounds obtained with the integrated process of the present invention can be advantageously added to any hydrocarbon mixture that can be used as fuel, in particular gasoil, gasoline, biodiesel, green diesel or mixtures thereof, and their addition allows, inter alia, a significant reduction in particulate emissions. In particular, said gasoil can be selected from gasoils falling within the specifications of gasoil for road transport according to the standard EN 590:2009, and also gasoils that do not fall within these specifications. Gasoil is generally a mixture containing hydrocarbons such as, for example, paraffins, aromatic hydrocarbons and naphthenes, typically having from 9 to 30 carbon atoms. The distillation temperature of gasoil generally ranges from 160° C. to 450° C. Said gasoil preferably has a density, at 15° C., determined according to the standard EN ISO 12185:1996/C1:2001, ranging from 780 kg/m$^3$ to 845 kg/m$^3$, preferably ranging from 800 kg/m$^3$ to 840 kg/m$^3$. The gasoil that can be used, can have a flash point, determined according to the standard EN ISO 2719: 2002, higher than or equal to 55° C., preferably higher than or equal to 65° C. The cetane number, determined according to the standard EN ISO 5165:1998, or the standard ASTM D6890:2008, can be higher than or equal to 47, preferably higher than or equal to 51. Gasoils that can be conveniently used can therefore be all known gasoils and can also derive from the mixing of diesel cuts of various origins and having varying compositions. The sulfur content in these diesel cuts preferably ranges from 2000 to 50 mg/kg, and even more preferably from 50 to 3 mg/kg.

Typical diesel cuts can be medium distillates, preferably having a boiling point ranging from 180 to 380° C. Examples of these cuts can be gasoils from primary distillation, gasoils from vacuum distillation, and from thermal or catalytic cracking, such as, for example, the desulfurized gasoil cut coming from fluid bed catalytic cracking (light cycle oil (LCO)), fuels from a Fischer-Tropsch process or of a synthetic origin. Cuts obtained from these after hydrogenation treatment can also be conveniently used. If the hydrocarbon mixture is a gasoline, gasolines characterized by a T95 (ASTM D86) not higher than 250° C., preferably not higher than 240° C., can be conveniently used, wherein T95 refers to the temperature at which 95% by volume of gasoline distills. Gasolines with a T95 lower than 250° C. are preferably used, in particular lower than 240° C., having a density ranging from 855 to 910 kg/m$^3$. Gasolines that can be conveniently used are those deriving from catalytic processes, preferably deriving from fluid-bed catalytic cracking processes (FCC), reforming processes, and mixtures thereof. In particular, HCN gasolines are therefore used, i.e. heavy gasolines (initial boiling point 150° C.) from FCC as such or desulfurized, and gasolines called Heavy Reformates, i.e. heavy gasolines (initial boiling point 150° C.) from reforming, or mixtures thereof. The sulfur content of these gasoline cuts preferably ranges from 2000 to 50 mg/kg, and even more preferably from 50 to 1 mg/kg.

If the components obtained with the integrated process of the present invention are used in compositions containing a biodiesel, as previously specified, said biodiesel comprises a mixture of fatty acid alkyl esters, in particular a mixture of fatty acid methyl esters (FAME) and can be produced starting from raw materials of a natural origin containing triglycerides. These raw materials as such, or the triglycerides obtained after subjecting said raw materials to separation, are subjected to a transesterification process in the presence of an alcohol, in particular methanol, and a catalyst, so as to obtain said fatty acid alkyl esters, in particular said fatty acid methyl esters (FAME). Further details relating to the production of biodiesel are described for example in Hanna et al., in the review "Biodiesel production: a review", published in "Bioresource Technology" (1999), vol. 70, pages 1-15. Preferably said biodiesel can be selected from those falling within the specifications of biodiesel for motor vehicles according to the standard EN 14214:2008.

The components obtained with the integrated process of the present invention can be used in compositions containing hydrotreated vegetable oils, called "green diesel": they are produced by the hydrogenation/deoxygenation of a material deriving from renewable sources such as, for example, soybean oil, rape oil, corn oil, sunflower oil, comprising triglycerides and free fatty acids, in the presence of hydrogen and a catalyst as described, for example, by Holmgren J. et al. in the article "New developments in renewable fuels offer more choices", published in "Hydrocarbon Processing", September 2007, pages 67-71.

The compositions which use the components obtained with the integrated process of the present invention are prepared by mixing the single components. Other possible additives present in the final composition can be introduced into both the final composition itself or into the hydrocarbon blend before their mixing.

Some illustrative and non-limiting examples are provided for a better understanding of the present invention and for its embodiment.

EXAMPLE 1

Etherification of Glycerine with Ethanol 10 cc of commercial resin Amberlyst 36 (Rohm and Haas, catalogue number 76079-A075C3A060) are charged into a fixed-bed reactor and the reactor is brought to a temperature of 145° C. A mixture of ethanol/glycerine (purity 99%) is then fed in a molar ratio of 10/1 at a space velocity of 0.3 hours$^{-1}$. The glycerine/ethanol reaction mixture is analyzed by means of mass GC indicating a conversion of glycerine equal to 71.18% and a selectivity to monoethoxy-propanediol equal to 91%, with the complement to 100% consisting of 8.88% of diethoxypropanol and 0.13% of triethoxypropane. The catalytic system proves to be stable for over 5,000 hours without any variation in the conversion and selectivity. The mixture resulting from the reaction is subjected to purification by means of distillation, the monoethoxy-propanediol obtained has a purity of 99%.

EXAMPLE 2

Reduction of Glycerine to 1,2-propanediol 10 cc of cupric chromite, a commercial product of Sigma-Aldrich (catalogue number 20,931-2), are charged into a fixed-bed reactor and the reactor is heated to a temperature of 250° C. by feeding pure hydrogen for 6 hours. The feeding of pure hydrogen is then interrupted and a mixture of pure glycerine (purity 99%) and hydrogen is fed in a glycerine/hydrogen molar ratio of 1/2 in moles at 250° C. and at a space velocity of 1 hour$^{-1}$. The total conversion of the glycerine is obtained, with a selectivity to 1,2-propanediol equal to 98%, with the complement to 100 consisting of propanol and hydroxyacetone. The catalyst proves to be stable under the reaction conditions for over 700 hours. The 1,2-propanediol obtained is purified by distillation, obtaining a product having a purity of 99.5%.

EXAMPLE 3

Dehydration of 1,2-propanediol to Propionic Aldehyde 10 cc of ZSM-5 zeolite in acid form (Zeolyst CBV 5524G-1822-18) are charged into a fixed-bed reactor and the reactor is heated to a temperature of 300° C. The 1,2-propanediol obtained from the previous reaction is then fed at a space velocity equal to 0.5 hours$^{-1}$. A complete conversion of 1,2-propanediol is obtained, with a selectivity equal to 83% to propionic aldehyde, with the complement to 100 consisting of acetone and propanol.

The propionic aldehyde thus obtained is purified by distillation from the other reaction products and half is destined for the reaction of Example 4 and the other half for the reaction of Example 5.

EXAMPLE 4

Synthesis of 2-ethyl-4-ethoxymethyl-1,3-dioxolane 10 cc of acid exchange resin Amberlyst 36 (Rohm and Haas, catalogue number 76079-A075C3A060) are charged into a fixed-bed reactor and a 1/1.05 mixture of monoethoxy-propanediol obtained in Example 1 and half of the propionic aldehyde obtained in Example 3 is fed at room temperature. The reaction mixture is fed at room temperature and at a space velocity equal to 5 hours$^{-1}$. A total conversion of the monoethoxy-propanediol fed is obtained, with a selectivity of 99% to the acetal 2-ethyl-4-ethoxymethyl-1,3-dioxolane. The acetal thus produced is then purified by distillation obtaining a product having a purity of 99%. The acetal thus obtained can be advantageously added to gasoil for the preparation of fuel compositions.

EXAMPLE 5

Transformation of Propionic Aldehyde to Propyl Propionate

Half of the quantity of propionic aldehyde obtained in Example 3 (50 g) is introduced into a three-necked glass flask, equipped with a cooler and mechanical stirrer. 0.5 g of aluminium isopropylate are then added and the mixture is stirred for 30 minutes at room temperature. The reaction is interrupted and the products obtained analyzed. The conversion of propionic aldehyde proves to be equal to 99% with a selectivity of 96% to propyl propionate. The propyl propionate thus obtained is separated from the reaction mixture by means of distillation. The propyl propionate can be advantageously used as component for gasolines.

The invention claimed is:

1. An integrated process for producing fuel components from glycerine, the process comprising purifying glycerine obtained from materials of biological origin to obtain a purified glycerine having a purity of at least 98%, and:
   (A) transforming a stream of the purified glycerine into an alkoxy-propanediol having formula: RO—CH$_2$—CHOH—CH$_2$OH, by etherification of the purified glycerine with an alcohol having formula ROH, wherein R is a C$_1$-C$_8$ alkyl, in the presence of an acid catalyst;
   (B) transforming another stream of the purified glycerine into 1,2-propanediol by reducing the purified glycerine with hydrogen in the presence of a reduction catalyst selected from the group consisting of copper chromite, a mixed chrome-zinc-copper oxide, a noble metal on coal, and a noble metal on iron oxide;
   (C) dehydrating the 1,2-propanediol obtained in the transforming (B), in the presence of a solid acid catalyst at a temperature ranging from 200 to 350° C. and a pressure ranging from 0.1 to 10 atmospheres, to obtain propionic aldehyde;
   (D) reacting part of the propionic aldehyde obtained in the dehydrating (C) with the alkoxy-propanediol obtained in the transforming (A), in the presence of an acid catalyst at a temperature ranging from −10 to 120° C.

and a pressure ranging from 0.1 to 20 atmospheres, to obtain an acetal having formula (a):

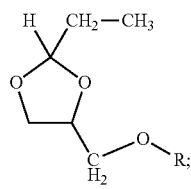

and (E) transforming a remaining part of the propionic aldehyde obtained in the dehydrating (C) to obtain a propyl propionate, by performing a Tishchenko reaction in the presence of a solid base catalyst.

2. The process according to claim 1, wherein:
R is selected from the group consisting of $CH_3$, $C_2H_5$, $C_3H_7$, $C_4H_9$, and $C_5H_{11}$; and
R' is selected from the group consisting of $CH_3$, $C_2H_5$, $C_3H_7$, $C_4H_9$, and $C_5H_{11}$.

3. The process according to claim 2, wherein R and R' are each independently selected from the group consisting of ethyl, n-propyl, iso-propyl, n-butyl, isobutyl, sec-butyl, tert-butyl, 3-methyl-1-butyl and 2-methyl-1-butyl.

4. The process according to claim 1, wherein the acid catalyst is selected from the group consisting of an acid exchange resin, an acid zeolite, a silico alumina and a supported phosphoric acid.

5. The process according to claim 1, wherein the transforming (A) is carried out at a temperature ranging from 50 to 200° C. and a pressure ranging from 1 to 20 atmospheres.

6. The process according to claim 1, wherein the transforming (B) is carried out at a temperature ranging from 100 to 300° C. under a hydrogen pressure ranging from 1 to 100 atmospheres.

7. The process according to claim 1, wherein the solid acid catalyst is selected from the group consisting of an alumina, a silico-alumina, a zeolite, cerium oxide (IV), thorium oxide and zirconia.

8. The process according to claim 1, wherein the acid catalyst in the reacting (D) is selected from the group consisting of an acid exchange resin, a zeolite and a silico alumina.

9. The process according to claim 1, wherein the solid base catalyst is selected from the group consisting of an aluminum alcoholate having formula: $Al(OR)_3$, wherein R is a linear or branched alkyl group ranging from $C_2$ to $C_6$, magnesium oxide, calcium oxide, strontium oxide, barium oxide, zinc oxide, a zeolite partially or fully exchanged with at least one alkaline metal, and a hydrotalcite having formula: $M^{2+}{}_a M^{3+}{}_2(OH)_{16} X \cdot nH_2O$, wherein $M^{2+}$ is a bivalent metal cation selected from the group consisting of $Mg^{2+}$, $Fe^{2+}$, $Ni^{2+}$, $Zn^{2+}$, $Cd^{2+}$ and $Co^{2+}$, $M^{3+}$ is a trivalent metal cation selected from the group consisting of $Al^{3+}$, $Fe^{3+}$, $Ga^{3+}$, $Cr^{3+}$, $Mn^{3+}$ and $Co^{3+}$, X is an anion selected from the group consisting of $CO_3{}^{2-}$, $OH^{3-}$ and $NO^{3-}$, and a is an integer ranging from 10 to 4.

10. The process according to claim 1, wherein the transforming (E) is carried out at a temperature ranging from −20 to 150° C. and a pressure ranging from 0.1 to 50 bar.

11. The process according to claim 1, wherein:
the glycerine obtained from materials of biological origin is glycerine comprising impurities of salts, water and optionally methanol; and
the purifying comprises:
removing the salts by treating the glycerine on at least one acid exchange resin; and
removing the water and optionally the methanol by fractionated distillation.

\* \* \* \* \*